United States Patent
Spannuth et al.

(10) Patent No.: US 10,132,764 B2
(45) Date of Patent: Nov. 20, 2018

(54) SYSTEM AND METHOD FOR RECONSTRUCTING THE SURFACE TOPOGRAPHY OF AN OBJECT EMBEDDED WITHIN A SCATTERING MEDIUM

(71) Applicant: Visuray Intech Ltd (BVI), Road Town, Tortola (VG)

(72) Inventors: Melissa Spannuth, Houston, TX (US); David Ponce, Randaberg (NO); Ådne Voll, Stavanger (NO); Henning Torsteinsen, Voll (NO); Morteza Esmaeili, Stavanger (NO); Spencer Gunn, London (GB)

(73) Assignee: Visuray Intech Ltd (BVI), Road Town (VG)

( * ) Notice: Subject to any disclaimer, the term of this patent is extended or adjusted under 35 U.S.C. 154(b) by 0 days.

(21) Appl. No.: 15/810,931

(22) Filed: Nov. 13, 2017

(65) Prior Publication Data
US 2018/0136146 A1    May 17, 2018

Related U.S. Application Data

(63) Continuation of application No. 14/268,821, filed on May 2, 2014.

(60) Provisional application No. 61/928,640, filed on Jan. 17, 2014.

(51) Int. Cl.
| | | |
|---|---|---|
| G01N 23/20 | (2018.01) | |
| G01T 1/16 | (2006.01) | |
| G01T 1/29 | (2006.01) | |
| G06T 15/04 | (2011.01) | |
| G01V 5/00 | (2006.01) | |
| G01V 5/12 | (2006.01) | |
| G01N 23/203 | (2006.01) | |
| G01T 1/164 | (2006.01) | |
| A61B 6/00 | (2006.01) | |
| G01N 23/046 | (2018.01) | |

(52) U.S. Cl.
CPC .......... *G01N 23/203* (2013.01); *G01N 23/20* (2013.01); *G01T 1/1645* (2013.01); *G01T 1/29* (2013.01); *G01T 1/2921* (2013.01); *G01V 5/0025* (2013.01); *G01V 5/12* (2013.01); *G06T 15/04* (2013.01); *A61B 6/483* (2013.01); *G01N 23/046* (2013.01); *G01N 2223/616* (2013.01)

(58) Field of Classification Search
CPC .. A61B 6/00; A61B 6/42; A61B 6/466; A61B 6/48; A61B 6/483; G01N 23/00; G01N 23/20; G01N 23/203; G01T 1/00; G01T 1/164; G01T 1/1641; G01T 1/1642; G01T 1/1645; G01T 1/29; G01T 1/2907; G01T 1/2914; G01T 1/2921; G01T 1/295; G06T 15/00; G06T 15/04; G06T 2200/00; G06T 2200/04; G06T 2200/08; A61K 47/48792; G01V 5/00; G01V 5/0025; G01V 5/12
See application file for complete search history.

*Primary Examiner* — Anastasia Midkiff
(74) *Attorney, Agent, or Firm* — Raymond R. Ferrera; Adams and Reese LLP

(57) ABSTRACT

Methods of reconstructing the surface topography of an object embedded in a scattering medium are provided, with example methodologies including: imaging an object embedded in a signal scattering medium using a scattered signal detector; detecting changes in the magnitude of a plurality of scattered signals obtained from multiple fields of view within the medium; and constructing an image of the surface topography of the object based on said plurality of detected signal magnitude changes. A plurality of system, apparatus, control means, evaluation methods, and materials and components useful for practicing the methods are also disclosed.

48 Claims, 5 Drawing Sheets

SYSTEM AND METHOD FOR RECONSTRUCTING THE SURFACE TOPOGRAPHY OF AN OBJECT EMBEDDED WITHIN A SCATTERING MEDIUM

FIELD

The present invention relates generally to the fields of imaging and logging the contents and characteristics of wells, boreholes and hydrocarbon foil cations, and in a particular though non-limiting embodiment to methods for constructing two- and three-dimensional images of objects embedded within a highly scattering medium and associated systems therefor.

BACKGROUND

X-ray backscatter imaging is a powerful tool for visualizing objects located behind optically opaque barriers when the object to be imaged is only accessible from one side. It is frequently used in security applications for screening packages, luggage, vehicles and people.

X-rays or other types of high energy penetrating radiation (e.g., gamma rays) are frequently used to investigate objects or structures located behind optically opaque barriers or embedded within opaque media. When both sides of the region of interest are accessible, including the object to be investigated, investigation can be performed using transmission imaging or radiography. An example of this type of imaging is a standard medical x-ray to investigate structures inside a human body.

When only one side of the region of interest is accessible, x-ray backscatter imaging can be used to create an image of the objects behind the opaque barrier. This technique is sometimes used for security screening of people and inspection of shipping containers.

X-ray backscatter imaging is most effective when the opaque barrier is relatively thin and the object to be imaged scatters strongly, as when searching for explosives in a vehicle. Backscatter imaging also works well when the object of interest scatters weakly but is set against a background that scatters strongly, as when searching for metal weapons concealed beneath clothing on a human. Backscatter imaging fails when the barrier is too thick and does not allow a sufficient number of x-rays to pass through.

In some cases, the object of interest is not simply situated in air behind an opaque barrier, but instead immersed in an opaque medium. For example, in an oil well the well fluids (e.g., hydrocarbons, drilling fluids, etc.) are generally opaque or of poor optical quality, thus seeing objects or parts of the well through these fluids is difficult. Another example is searching for objects buried in the ground, such as landmines or improvised explosive devices. In these situations, the medium is effectively a barrier and, if x-rays can penetrate the medium material, x-ray backscatter imaging can allow one to create an image of the object.

However, if the medium scatters too strongly, then the signal from the medium itself can be greater than the signal from the object. This reduces contrast in the image and obscures detail on the object. Various image processing techniques can be applied to mitigate the influence of the medium scattering and obtain acceptable images. In a very strongly scattering medium, the signal from the medium may completely overwhelm the signal from the object. In that case, scattering from the medium must be suppressed through specific design of the imaging apparatus. Alternately, the large signal from the medium can be embraced and used to determine the distance to the surface of the object.

For each of these modes, the prior art teaches only limited methods of investigation and relatively unsophisticated apparatus to practice those methods, but in all such cases the resulting images or data provide little to no information about the distance to the target object or its depth within the opaque medium.

Furthermore, radiography techniques require access to both sides of the region of interest as the radiation source and detector must be positioned such that transmission through both the object and the medium can be measured. Backscattering techniques avoid this limitation, but will fail or be of only limited use when the medium scatters very strongly, as scattering from the medium will overwhelm the scattering from the object, thereby leading to poor image quality.

For obtaining three-dimensional representations of materials or locating objects within a medium, x-ray computed tomography is a very well-known technique. Again, the prior art relates to methods and apparatus for practicing x-ray computed tomography. However, this technique also requires access to multiple sides of the region of interest because it is premised on the taking of multiple radiography measurements.

In recognition of this deficiency, a number of techniques have been developed that provide three-dimensional or depth information for objects located behind or embedded within an opaque material when the region of interest is accessible from only one side. One such technique is Compton backscatter tomography (CBT) as described by Zhu et al. in *Measurement Science and Technology* (1996).

In CBT, attenuation of radiation along a scattering path is measured and algorithms similar to those used in conventional x-ray computed tomography are applied to create a three-dimensional reconstruction of the entire region-of-interest.

As a variation on the general CBT technique, Faust (US 2004/0218714) teaches a method and apparatus that uses a coded aperture to image a buried landmine or improvised explosive device. The method produces slices at different depths within the region of interest because the size of the image projected through the coded aperture depends upon the depth at which the photons forming the image originated.

Another variation on CBT is taught by Shedlock, Meng, Sabri, Dugan and Jacobs (US 2011/0200172). This method and apparatus scans a fan-shaped beam across a region of interest and uses algebraic reconstruction or back projection techniques to generate an image. When the scanning is arranged so that a number of scan paths overlap, three-dimensional information about the object or medium can be obtained in the regions of overlap.

Yet another variation on CBT is taught by Annis (U.S. Pat. No. 7,620,150) in a system for backscatter imaging of objects at shallow depths, especially in human skin. The method involves scanning multiple beams of radiation across the region-of-interest and collecting the scattered radiation. Image contrast is created by differences in attenuation and density of the material along the beam path. By moving the source to different locations and using standard image combination techniques, the method can produce three-dimensional tomography images.

Another technique for obtaining depth information is to use x-ray photons having different energies. Higher energy photons penetrate more deeply into the object or medium under investigation. Therefore, scattered photons with low energy are more likely to have scattered from material at shallow depths, whereas scattered photons with high energy are more likely to have scattered from material at deeper depths.

Grodzins and Adams (U.S. Pat. No. 6,424,695) determine the depth of an object behind an opaque barrier using a source x-ray beam and two or more detectors located at different distances from the beam axis. In this arrangement, detectors furthest from the beam axis receive more scattering originating from deeper portions of the region of interest as a proportion of the total amount of scattering than do detectors closer to the beam axis. This occurs because the solid angle viewed by a far detector is large for deep portions and small for shallow portions, whereas the opposite is true for a close detector. The result is that closer detectors preferentially image shallow objects and farther detectors preferentially image deeper objects.

Morton (US 2012/0134473) uses a pulsed x-ray beam and measures the time delay between the outgoing pulse and when the scattered signal arrives at the detector. By scanning the beam across the region of interest, this technique creates a three-dimensional map of the surface of the object under investigation and works reasonably well for detecting weakly-scattering objects embedded within highly-scattering media.

In a rather different approach, Penny and Valentine (U.S. Pat. No. 8,314,394 and U.S. Pat. No. 8,426,822) create photons for imaging via positron-electron annihilation. This process creates two photons travelling in opposite directions. If one of these photons is detected near the annihilation event, then the direction of the second photon is known. When photons scattered within the region of interest are detected, they can be correlated with the outgoing photons so that the exact trajectory of each photon through the material is known.

Furthermore, multiply-scattered photons can be filtered out on the basis of their significantly lower energy. In this manner, the technique provides three-dimensional information about the scattering properties of the material.

Finally, Wood (U.S. Pat. No. 8,433,037) teaches an x-ray radar technique for generating three-dimensional information about a target object. Outgoing x-rays are created with a radio-frequency modulation using a radio-frequency modulated electron beam passed across a micro-channel plate. The modulation persists in the backscattered x-rays, and strikes a scintillator or the like to produce visible photons. The scintillation photons are then amplified by the micro-channel plate before striking the detector. The contrast on the detector represents the magnitude of the difference between the radio-frequency phase bias on the micro-channel plate and the radio-frequency modulated backscattered x-rays. By acquiring a subsequent frame with a 90° phase shift on the micro-channel plate, the technique generates three-dimensional information. The ratio of the two 90° phase-shifted frames gives a value proportional to the range, and calculating the arctangent of this ratio will provide reasonably precise range increments.

In view of the foregoing there is plainly a longstanding but currently unmet need for durable, flexible, time- and cost-effective methods and means of constructing two- and three-dimensional images of objects embedded within signal scattering media that overcome the shortcomings of the prior art and admit to meaningful evaluation of otherwise difficult to assess subject topographies.

SUMMARY

Methods of reconstructing the surface topography of an object embedded in a scattering medium are provided, with example methodologies including: imaging an object embedded in a signal scattering medium using a scattered signal detector; detecting changes in the magnitude of a plurality of scattered signals obtained from multiple fields of view within the medium; and constructing an image of the surface topography of the object based on said plurality of detected signal magnitude changes. A plurality of system, apparatus, control means, evaluation methods, and materials and components useful for practicing the methods are also disclosed.

DETAILED DESCRIPTION

Figure 1:
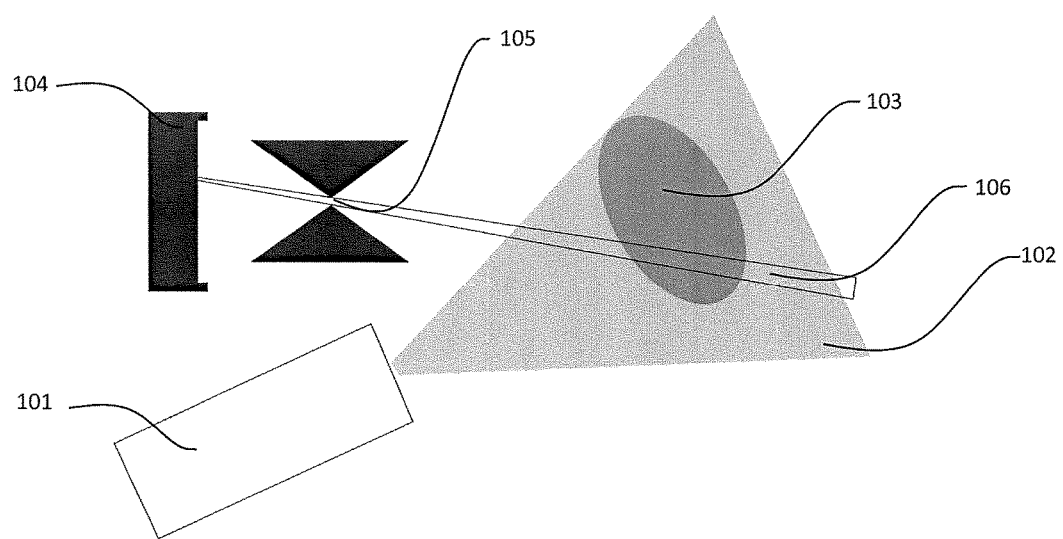
FIG. 1 is a schematic diagram of an example system suitable for carrying out the image detection and construction methods disclosed and claimed herein.

The instant description generally discloses techniques useful for creating two- and three-dimensional representations of highly-absorbing, weakly-scattering objects embedded within a highly-scattering medium using x-ray back scattering from the medium.

The technique relies upon changes in the magnitude of the scattering signal from the medium as the distance from the detector to the object varies. In this manner, the surface topography of the object is discernible from the different signal magnitudes registered by different detector fields of view, which are then constructed and displayed as a two-dimensional image. By calibrating signal magnitudes from each field of view with known distances, the scattering signals from an unknown object can be converted into distances and displayed as a three-dimensional reconstruction.

Accordingly, a specific though non-limiting example method of reconstructing the surface image of an object embedded in a scattering medium comprises: imaging a highly-absorbing, weakly-scattering object embedded in a highly scattering medium using a scattered signal detector; detecting changes in the magnitude of a plurality of scattering signals obtained from multiple fields of view within the medium as the plurality of field of view signal magnitudes vary; constructing a two-dimensional image of the surface topography of the object based on the plurality of detected signal magnitude changes; calibrating signal magnitudes obtained from a plurality of known field of view images as compared to detected scattering signal magnitudes obtained from the object; and converting calibrated signal magnitudes into distances and reconstructing a three-dimensional image representative of the surface topography of the embedded object, or a three-dimensional solid representation of the embedded object.

Also provided are various apparatus useful for practicing the technique. While those of ordinary skill in the art will readily appreciate that there are many possible embodiments for the apparatus, all must possess a minimum set of features in order to effectively practice the technique.

In one non-limiting embodiment, the apparatus comprises: a means for imaging a highly-absorbing, weakly-scattering object embedded in a highly scattering medium using a scattered signal detector; a means for detecting changes in the magnitude of a plurality of scattering signals obtained from multiple fields of view within the medium as the plurality of field of view signal magnitudes vary; a means for constructing a two-dimensional image of the surface topography of the object based on the plurality of detected signal magnitude changes; a means for calibrating signal magnitudes obtained from a plurality of known field of view images as compared to detected scattering signal magnitudes obtained from the object; and a means for converting calibrated signal magnitudes into distances and reconstructing a three-dimensional image representative of the surface topography of the embedded object.

In addition, the scene to be imaged should also possess certain properties. For example, a simple apparatus and scene possessing all the necessary qualities is assumed in FIG. 1, which shows a schematic diagram of an appropriate configuration. First, the apparatus must contain a radiation source capable of illuminating the entire region of interest; in FIG. 1 the representative example source is an x-ray source, though sources of other electromagnetic radiation spectra will also suffice.

The description of the method provided below assumes the region is illuminated by a relatively stationary flood, or very wide angle, source, though those of skill in the art will appreciate that the method can also be practiced with any variety of scanning beam, such as a pencil beam, fan beam, wedge beam, etc.

Throughout this description, the radiation source will be referred to as 'x-rays' although any type of radiation with sufficient energy to penetrate the necessary distance through the medium can be used effectively. For the scene described below, hard x-rays with energy in the range from 50 to 250 keV are appropriate. However, such x-rays could be substituted with radiation having any energy outside of the visible light range, such as microwaves, infrared radiation, ultraviolet radiation or gamma rays.

Next, the medium surrounding the object should scatter the radiation source relatively strongly, while not absorbing the radiation too strongly. If absorption in the medium is too strong, not enough x-rays will penetrate the full distance to the object and the depth of view will be limited. Consequently, the object should absorb strongly in order to stop x-rays from traveling through the object to the medium behind it.

The object can be either a strong or weak scatterer of x-rays, though a weakly-scattering object is generally preferred. If the scattering from the object is too strong, then its signal can be on par with that from the medium, especially when the object is close to the detector. This situation will result in poor contrast and a distorted reconstruction. However, as the object absorbs strongly, the signal from the object will be much smaller than that from the medium.

One non-limiting example of a highly-absorbing, weakly-scattering object within a strongly-scattering medium is a steel object disposed in water or a water-hydrocarbon mixture.

Though steel scatters more strongly per unit volume than water (due to the higher electron density of the steel), steel will also absorb more strongly. The stronger absorption means that only a very small portion of the surface of a steel object contributes significantly to the scattering from the object, thereby resulting in a relatively small effective scattering volume.

The weak x-ray absorption in water means that the x-rays will penetrate deeper, thereby resulting in a larger effective scattering volume. Overall, water with a depth of about 1 cm will scatter more strongly than a thick steel object. Thus, steel in water is a good system for applying the present technique.

The final requirement for the apparatus is a detection system having a limited field of view but an ability to observe the entire region of interest. In addition, the detector should be positioned outside the source area of illumination so as to receive only backscattered x-rays and not transmitted x-rays.

The description below assumes that this is achieved using a pixelated detector and a pinhole to limit the region from which scattering enters each pixel. By appropriate selection of the pinhole opening angle and position, the entire region of interest can be projected onto the detector. By choosing a sufficiently small diameter for the pinhole opening, the width of the field of view for each pixel can be sufficiently small to achieve good spatial resolution of the object.

Other types of detection systems may be advantageous in certain applications of this method. For example, a position-sensitive detecting device, such as an Anger camera, can be substituted for the pixilated detector. Furthermore, a coded aperture can be used in place of the pinhole. Alternately, when combined with a scanning radiation beam, strip-based segmented detectors or non-pixelated detectors, each configured to provide appropriate collimation, will prove equally useful. Multiple detector systems can also be monitored by control systems so that specific detector responses within the systems can be isolated, and emphasized (or de-emphasized) in the object topography evaluation process.

Furthermore, by incorporating multiple detectors placed in various locations around the source, the region of interest can be viewed from multiple angles. This could help alleviate problems associated with regions of the object being obscured by features of the object topography. In addition, overlapping a plurality of fields of view obtained from multiple detectors will provide additional information to aid in refinement of the final image or reconstruction.

Any apparatus constructed to practice this technique will most likely include more components than those listed above. However, the typical apparatus will include at least a source to illuminate the entire region of interest; a highly-absorbing object embedded in a highly-scattering medium; and a detection system with many detection elements, each having a limited field of view.

These requirements ensure that the detector system receives sufficient signal response as to create a good depth contrast; that the scattering registered by the detectors originates primarily from the medium; and that there is good lateral coverage on the object surface.

Those skilled in the art will recognize that there may be many ways to realize these requirements. For the purpose of explaining the present invention, however, the apparatus is assumed to be a flood illumination source with a pixel detector and pinhole system viewing a steel object in water, but any number of alternative means and configurations will suffice so long as they satisfy the basic requirements referenced above.

The physical principles underlying this invention are illustrated in FIG. 1, which schematically depicts the amount of medium material that contributes to the signal registered by a single pixel for different distances relative to a flat object. When the object is close to the source and detector, the amount of medium contributing to the scattering signal recorded by the detector is small. As the distance from the source and detector to the object increases, the amount of intervening medium material increases and hence the backscattered signal also increases.

Figure 3:
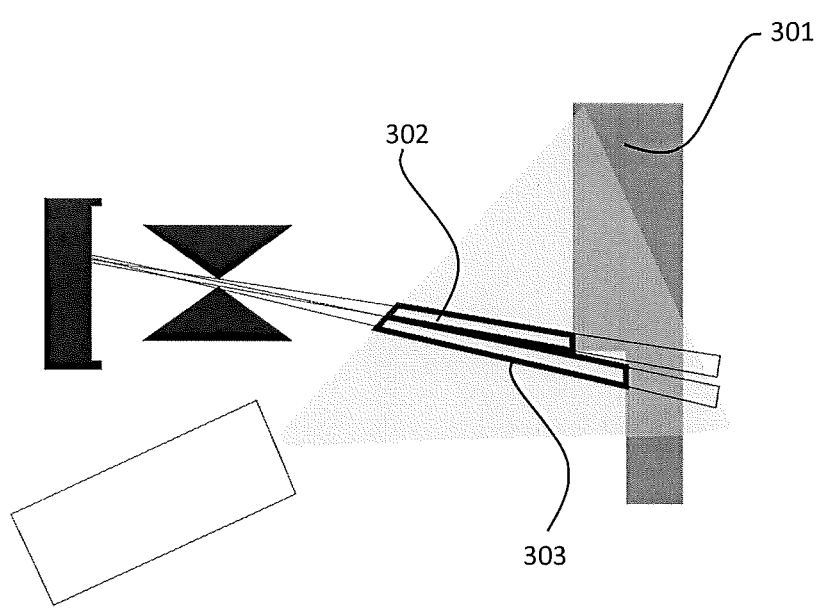
FIG. 3 is a representative depiction of the difference in the amount of intervening material between two adjacent pixels and corresponding portions of the surface of an object that each pixel views.

Similarly, two pixels will register different amounts of scattering due to differences in distance to the object arising from surface topography. See, for example, the representative embodiment depicted in FIG. 3. Adjacent pixels 1 and 2 view regions of the object surface on either side of a step in the surface topography. Clearly, pixel 1, which views the closer side of the step, has much less material intervening between the detector and the object, whereas pixel 2, which views the further side of the step, has much more material between the detector and the object. As a result, pixel 2 will register a larger amount of backscattering than pixel 1.

Following this logic, all of the pixels having a field of view that encompasses the closer side of the step will be dimmer than pixels having a field of view that encompass the further side of the step. Displaying the signals registered by all of the pixels as an array produces a type of two-dimensional image where differences in brightness reflect the topography of the object surface.

Figure 4:
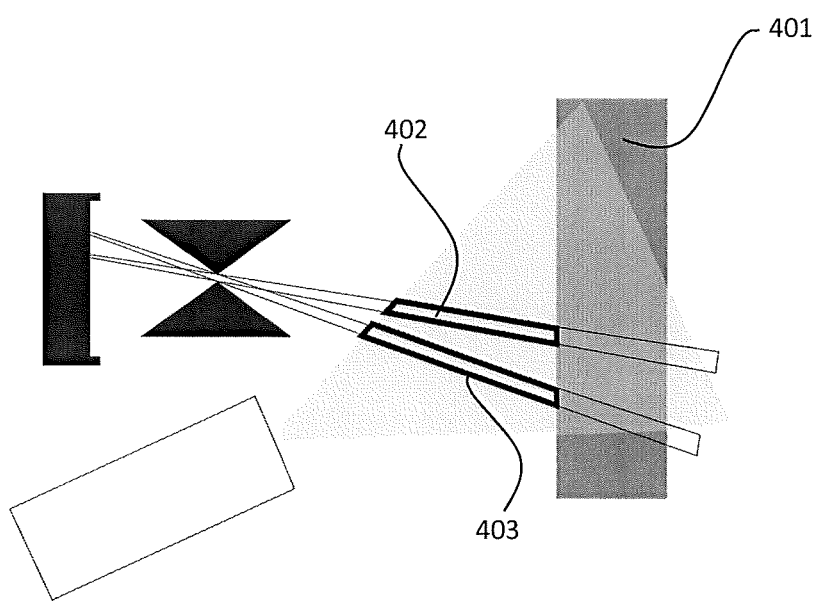
FIG. 4 is a representative depiction of the difference in the amount of material within the field of view of different pixels for a flat object.
Figure 5:
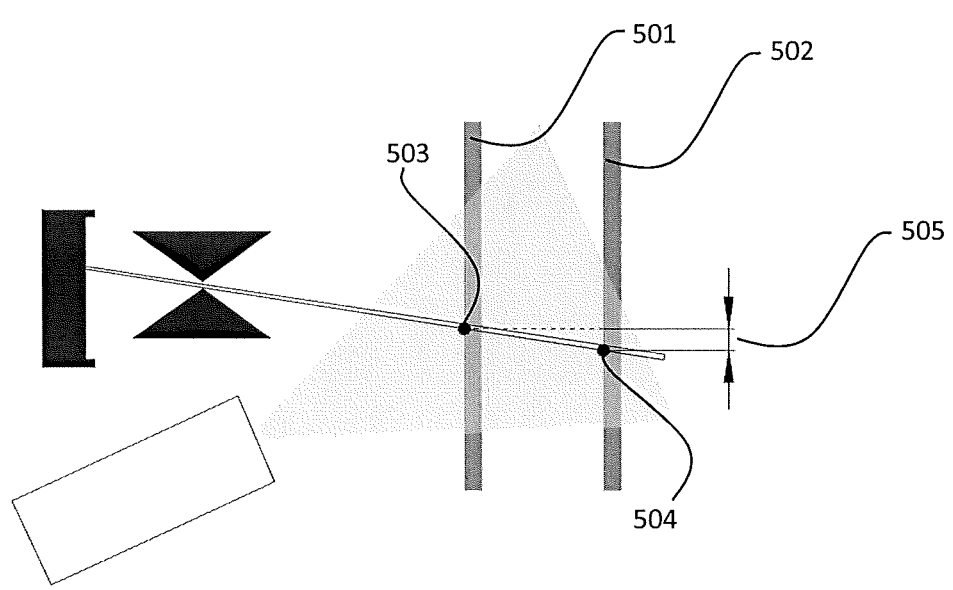
FIG. 5 is of the difference in lateral position at which the field of view of a pixel intersects the object depending upon the object distance.

In order to improve the contrast in the image and ease interpretation, the image may need to be corrected for flat-field distortions. As depicted in FIG. 4, these distortions arise because the amount of material within the pixels FOV can vary even for a flat object. In the typical case, the field of view for pixel 1 intersects the object much closer to the detector resulting in a smaller amount of material within the field of view, whereas the field of view for pixel 2 has such a steep angle that it intersects the object further from the detector, thereby resulting in a larger amount of material within the field of view.

The net result of this arrangement is that pixel 2 will register a larger backscattering signal than pixel 1, even though the object is flat and substantially parallel to the source detector plane. In the scheme described in the previous paragraph, this difference in signal would be interpreted as a false surface topography of the object.

In order to mitigate this discrepancy, a flat-field correction can be applied to the data as received from the detectors. In one example embodiment, the flat-field correction is performed empirically using an image of a known flat object, or, in an alternative embodiment, theoretically by calculating the anticipated differences in the field of view of the pixels when intersected by a flat object. Alternately, the correction can be performed semi-empirically, for example, by using images of a flat object to fit a theoretical model.

Those of ordinary skill in the art will readily appreciate that there are many other possible ways to achieve the flat-field correction, and that there are also other types of corrections that can be performed to improve the image quality (e.g., offset correction, gain correction, background subtraction or division, etc.). Furthermore, many standard image processing techniques, such as enhancement or filtering as well as image analysis techniques, can be applied to the resulting image without departing from the scope of the instant disclosure.

In addition to a two-dimensional image, the technique can also produce a three-dimensional reconstruction of the object using a depth calibration and the geometry of the apparatus. The purpose of the calibration is to compare and convert the signal recorded by each field of view of the detector system arrangement into a physical distance from some fixed reference point to the portions of the object viewed by each field of view.

Ordinarily skilled artisans will appreciate there are many possible ways to achieve this calibration, so only a few representative examples will be discussed herein. For the purpose of this example, the x-ray source is assumed to be the fixed reference point against which such distances are measured.

In some embodiments, one type of calibration involves a look-up table created by measuring the backscattering signal from a flat object at several distances. The flat object, for example a steel plate at least 3 cm thick, is positioned in the medium substantially parallel to the plane of the source at several known distances. At each distance, the signal registered by the detector is recorded and stored in the look-up table along with the corresponding distance. When the scattering from an unknown image is recorded, the signal from each pixel is compared with the values in the look-up table and the corresponding distance determined.

Determination of the correspondence can be carried out in several ways, for example linear interpolation between consecutive distance points in the look-up table, non-linear interpolation, or nearest-neighbor look-up. Alternately, a function could be fit to the look-up table data for each pixel and the function used to determine distance. Other methods will be evident to those of skill in the art.

Another type of calibration starts from a theoretical point of view, but uses empirical data to fit the theoretical model. A composite model can then be developed that considers the scattering and attenuation of the medium and results in an estimate relating distance and scattering signal. Depending upon the necessary depth resolution and the accuracy of the scattering measurements by the detector, a single equation that can be developed for all pixels, or individual equations for each pixel taking into account differences in the field of view, may be used.

Such equations may have some free parameters that can be determined from measurements of the scattering signal from a flat object positioned as described above at one or more known distances. In any event, the result of the calibration is that each pixel, or detector field of view, has a distance relative to the portion of the object within each field of view with which it is associated.

Figure 2:
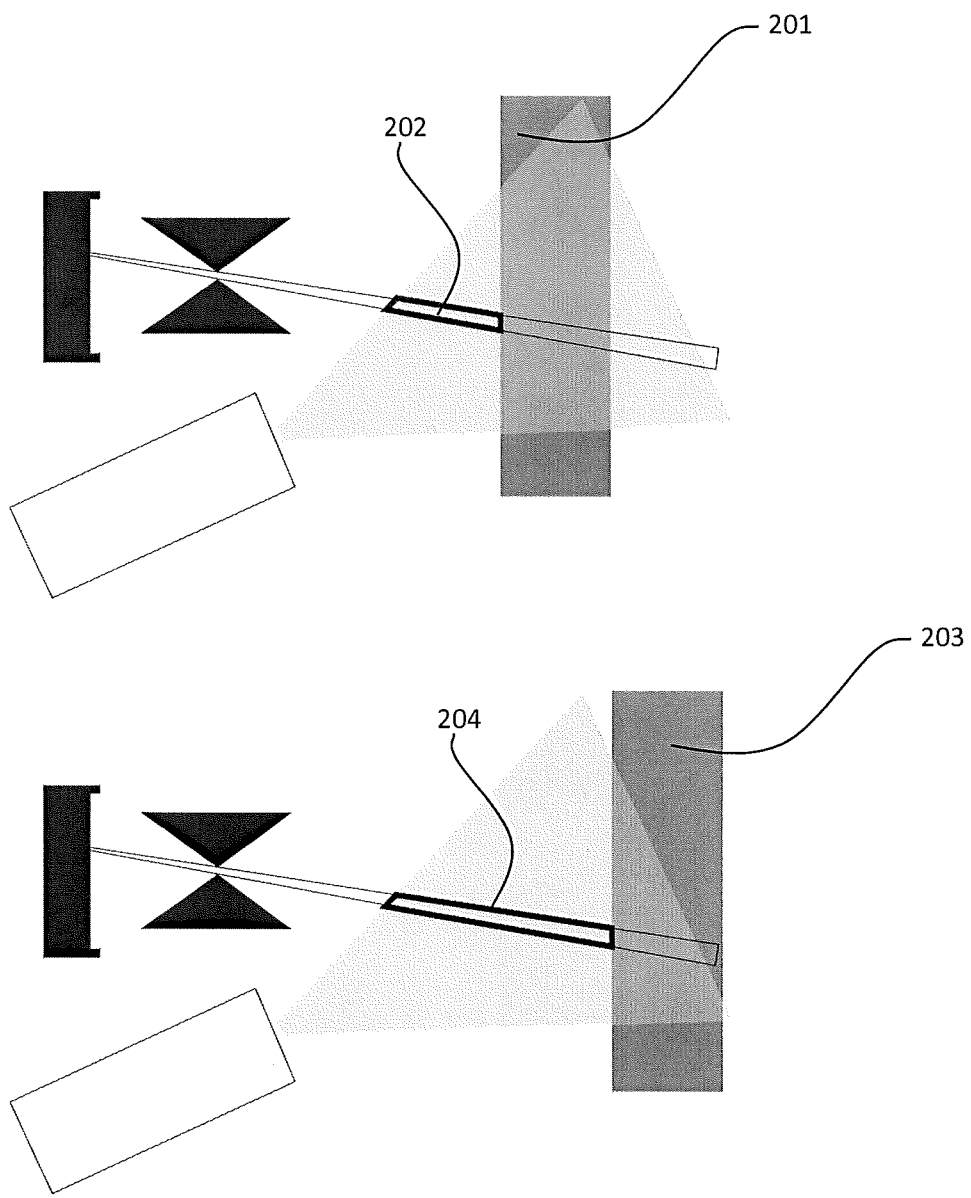
FIG. 2 is an illustrative example of the physical principles underlying the image detection and construction methods disclosed and claimed herein.

Once the mentioned distances are established, they are projected into corresponding lateral positions in order to create an accurate reconstruction of the object. See, for example, the embodiment depicted in FIG. 2.

The diagram shows that for a single detector field of view, the lateral position at which the field of view intersects the object (i.e., the position in the plane parallel to the plane of the source) varies depending upon the distance to the object. In this example, the intersection point with a shallower object is laterally closer to the object than that with a deeper object.

In this embodiment the precise details of the projection will depend upon the particular apparatus used, and especially the detection system. In the case of a pixilated detector and pinhole system, the projection can be as simple as the equation for a line in three dimensions that passes through the center of a given pixel and the center of the pinhole. Once a depth coordinate is determined from the calibration, the two lateral coordinates are determined from the equation of the line. Alternate projection methods will be evident to those skilled in the art, and include backwards projection of voxels in the object space onto detector pixels, methods that account for overlapping detector fields of view, and methods that integrate signals from multiple detector systems.

The result of the calibration and projection is a set of corresponding coordinates in three dimensions that describe the locations of portions of the surface topography of the object. These coordinates are then displayed using one or more known means. One option is a three-dimensional rendering of the surface, or a surface plot. If the sides of the object are visible, the invisible portions of the object can be interpolated by some appropriate scheme to create a three-dimensional volume.

The reconstructed volume data is then rendered on a computer monitor or other output device, printed using a three-dimensional printer, etc., for visualization purposes. Each of the aforementioned options and many others will admit to a reconstruction that can be rotated and viewed from multiple angles or viewpoints. If the maneuverability is not necessary, then the coordinate set can be plotted as a two-dimensional topographic map of the surface or a two-dimensional image with depth represented by different colors or shades of grey.

Many other display options will be evident to those skilled in the art. In all cases, though, the key element that makes the reconstruction possible is the correspondence between the backscattering signal from the medium and the depth to the object.

The foregoing description has taught the various elements necessary to create a representation of a highly-absorbing object embedded within a highly-scattering medium using x-ray backscattering from the medium. The technique relies upon changes in the magnitude of the scattering signal from the medium as the distance from the detector to the object varies.

Thus, the surface topography on the object is derived from the different signal magnitudes registered by the different fields of view of the detector system arrangement. The output display result is either a two-dimensional image or, after calibration, a three-dimensional reconstruction.

An exemplary method for practicing this technique would involve at least the steps of collecting the backscattered x-ray signal for some amount of time; transferring the signal from the detector to an image display device; and displaying the magnitude of the signal with any necessary adjustments or enhancements to optimize viewing.

Alternatively, the method includes calibrating backscattered signal to object distance; collecting the backscattered x-ray signal for a defined period of time; transferring the signal from the detector to a data processing device; using the calibration to correlate signal magnitude with object depth; projecting the individual fields of view to their appropriate lateral positions; and displaying the resulting depth map with any necessary adjustments or enhancements to optimize viewing.

Many variations of these methods will be evident to those skilled in the art. For example, the backscattered x-ray signal can be collected in a photon counting mode or energy integration mode and then collected in a single exposure of the detector or in multiple exposures that are later summed, averaged or otherwise combined. The scattered x-ray signal can alternately be divided among multiple energy ranges, each of which is analyzed separately or in comparison to one another.

Additionally, a background signal representing all photons not originating from the region of interest can first be measured and then subtracted from all other signal measurements. Furthermore, the reconstruction and display steps can be modified to incorporate data from overlapping fields of view from multiple detectors or multiple pixels on a single detector.

While the specific embodiments discussed in this disclosure involve x-rays and x-ray backscattering, it will be evident to ordinarily skilled artisans that the technique can be practiced with other types of radiation as well. Even more generally, the fundamental concept can be applied in any situation where an object of interest is embedded within a medium from which an external stimulus can elicit some response.

The response from the medium must be measureable and proportional to the amount of material within the region over which the measuring device is sensitive. The response from the object, if present, will optimally be much less than the response from the medium. The device for measuring the response should be sensitive to a relatively small volume within the region of interest in order to obtain a good spatial resolution in the reconstruction of the object.

The foregoing specification is provided for illustrative purposes only, and is not intended to describe all possible aspects of the present invention. Moreover, while the invention has been shown and described in detail with respect to several exemplary embodiments, those of skill in the pertinent arts will appreciate that minor changes to the description and various other modifications, omissions and additions may be made without departing from the scope thereof.

The invention claimed is:

1. A method of reconstructing a two-dimensional representation of a surface topography of an object disposed in a scattering medium, the method comprising:
   (a) acquiring a plurality of scattered signals from multiple regions of the scattering medium and an object disposed in said scattering medium using a scattered signal detector;
   (b) detecting differences among the magnitudes of said plurality of scattered signals obtained from said multiple regions of the scattering medium;
   (c) correlating differences among the magnitudes of said plurality of scattered signals obtained from said multiple regions with differences in the amount of scattering medium interposed between the object and the scattered signal detector among said multiple regions;
   (d) correlating differences in the amount of scattering medium interposed between the object and the scattered signal detector among said multiple regions with differences in the distance between the object and the scattered signal detector among said multiple regions; and
   creating a two-dimensional representation of the surface topography of the object using the magnitudes of the plurality of scattered signals correlated to differences in the distance between the object and the scattered signal detector.

2. The method of claim 1, further comprising: reconstructing a two-dimensional representation of the surface topography of an object having a scattered signal magnitude either less than the scattered signal magnitude of the scattering medium or greater than the scattered signal magnitude of the scattering medium.

3. The method of claim 1, further comprising: creating a two-dimensional representation of the surface topography of a solid object.

4. The method of claim 1, further comprising: creating a two-dimensional representation of the surface topography of an object disposed in a scattering medium comprising a single phase fluid.

5. The method of claim 1, further comprising: creating a two-dimensional representation of the surface topography of an object disposed in a scattering medium comprising a multi-phase fluid.

6. The method of claim 1, further comprising: acquiring a plurality of scattered signals from multiple regions of a scattering medium and an object disposed in the scattering medium using an electromagnetic scattered signal detector.

7. The method of claim 1, further comprising: acquiring a plurality of scattered signals from multiple regions of a scattering medium and an object disposed in the scattering medium using an x-ray scattered signal detector.

8. The method of claim 1, further comprising: acquiring a plurality of scattered signals from multiple regions of a scattering medium and an object disposed in the scattering medium using a pixelated detector.

9. The method of claim 1, further comprising: acquiring a plurality of scattered signals from multiple regions of a scattering medium and an object disposed in the scattering medium using an Anger camera.

10. The method of claim 1, further comprising: acquiring a plurality of scattered signals from multiple regions of a scattering medium and an object disposed in the scattering medium using a plurality of scattered signal detectors.

11. The method of claim 1, further comprising: detecting differences in the magnitudes of a plurality of scattered signals obtained from an electromagnetic signal source disposed in communication with a plurality of pinhole apertures.

12. The method of claim 1, further comprising: detecting differences in the magnitudes of a plurality of scattered signals obtained from an electromagnetic signal source disposed in communication with a plurality of coded apertures.

13. A system for reconstructing a two-dimensional representation of a surface topography of an object disposed in a scattering medium, the system comprising:
  (a) an acquisition system used to acquire a plurality of scattered signals from multiple regions of the scattering medium and an object disposed in said scattering medium;
  (b) a magnitude difference detector used to detect differences among the magnitudes of said plurality of scattered signals obtained from said multiple regions of the scattering medium;
  (c) a magnitude correlation system used to correlate differences among the magnitudes of said plurality of scattered signals obtained from said multiple regions with differences in the amount of scattering medium interposed between the object and the scattered signal detector among said multiple regions;
  (d) a correlation system used to correlate differences in the amount of scattering medium interposed between the object and the scattered signal detector among said multiple regions with differences in the distance between the object and the scattered signal detector among said multiple regions; and
  (e) a two-dimensional representation creation system used to create a two-dimensional representation of the surface topography of the object using the magnitudes of the plurality of scattered signals correlated to differences in the distance between the object and the scattered signal detector.

14. The system of claim 13, further comprising: a two-dimensional representation creation system for creating a two-dimensional representation of the surface topography of an object having a signal scattering magnitude either less than the scattered signal magnitude of the scattering medium or greater than the scattered signal magnitude of the scattering medium.

15. The system of claim 13, further comprising: a system for reconstructing a two-dimensional representation of a surface topography of a solid object.

16. The system of claim 13, further comprising: a system for reconstructing a two-dimensional representation of a surface topography of an object disposed in a scattering medium comprising a single phase fluid.

17. The system of claim 13, further comprising: a system for reconstructing a two-dimensional representation of a surface topography of an object disposed in a scattering medium comprising a multi-phase fluid.

18. The system of claim 13, further comprising: an acquisition system used to acquire a plurality of scattered signals from multiple regions of the scattering medium and an object disposed in said scattering medium using an electromagnetic signal scattering detector.

19. The system of claim 13, further comprising: an acquisition system used to acquire a plurality of scattered signals from multiple regions of the scattering medium and an object disposed in said scattering medium using an x-ray signal scattering detector.

20. The system of claim 13, further comprising: an acquisition system used to acquire a plurality of scattered signals from multiple regions of the scattering medium and an object disposed in said scattering medium using a pixelated detector.

21. The system of claim 13, further comprising an acquisition system used to acquire a plurality of scattered signals from multiple regions of the scattering medium and an object disposed in said scattering medium using an Anger camera.

22. The system of claim 13, further comprising: an acquisition system used to acquire a plurality of scattered signals from multiple regions of the scattering medium and an object disposed in said scattering medium using a plurality of signal scattering detectors.

23. The system of claim 13, further comprising: a magnitude difference detector for detecting differences in the magnitudes of a plurality of scattered signals obtained from an electromagnetic signal source disposed in communication with a plurality of pinhole apertures.

24. The system of claim 13, further comprising: a magnitude difference detector for detecting differences in the magnitudes of a plurality of scattered signals obtained from an electromagnetic signal source disposed in communication with a plurality of coded apertures.

25. A method of reconstructing a three-dimensional representation of a surface topography of an object disposed in a scattering medium, the method comprising:
  (a) acquiring a plurality of scattered signals from multiple regions of the scattering medium and an object disposed in said scattering medium using a scattered signal detector;
  (b) detecting differences among the magnitudes of said plurality of scattered signals obtained from said multiple regions of the scattering medium;
  (c) correlating differences among the magnitudes of said plurality of scattered signals obtained from said multiple regions with differences in the amount of scattering medium interposed between the object and the scattered signal detector among said multiple regions;
  (d) correlating differences in the amount of scattering medium interposed between the object and the scattered signal detector among said multiple regions with differences in the distance between the object and the scattered signal detector among said multiple regions;

(e) creating a calibration between the magnitude of a scattered signal and a distance between the object and the scattered signal detector;

(f) converting each of said plurality of scattered signal magnitudes into distances between the object and the scattered signal detector; and (g) creating a three-dimensional representation of the surface topography of the object using the magnitudes of the plurality of scattered signals calibrated to the distance between the object and the scattered signal detector.

26. The method of claim 25, further comprising: reconstructing a three-dimensional representation of the surface topography of an object having a scattered signal having a magnitude either less than the scattered signal of the scattering medium or greater than the scattered signal of the scattering medium.

27. The method of claim 25, further comprising: creating a three-dimensional representation of the surface topography of a solid object.

28. The method of claim 25, further comprising: creating a three-dimensional representation of the surface topography of an object disposed in a scattering medium comprising a single phase fluid.

29. The method of claim 25, further comprising: creating a three-dimensional representation of the surface topography of an object disposed in a scattering medium comprising a multi-phase fluid.

30. The method of claim 25, further comprising: acquiring a plurality of scattered signals from multiple regions of a scattering medium and an object disposed in the scattering medium using an electromagnetic scattered signal detector.

31. The method of claim 25, further comprising: acquiring a plurality of scattered signals from multiple regions of a scattering medium and an object disposed in the scattering medium using an x-ray scattered signal detector.

32. The method of claim 25, further comprising: acquiring a plurality of scattered signals from multiple regions of a scattering medium and an object disposed in the scattering medium using a pixelated detector.

33. The method of claim 25, further comprising: acquiring a plurality of scattered signals from multiple regions of a scattering medium and an object disposed in the scattering medium using an Anger camera.

34. The method of claim 25, further comprising: acquiring a plurality of scattered signals from multiple regions of the scattering medium and an object disposed in the scattering medium using a plurality of scattered signal detectors.

35. The method of claim 25, further comprising: detecting differences in the magnitudes of a plurality of scattered signals obtained from an electromagnetic signal source disposed in communication with a plurality of pinhole apertures.

36. The method of claim 25, further comprising: detecting differences in the magnitudes of a plurality of scattered signals obtained from an electromagnetic signal source disposed in communication with a plurality of coded apertures.

37. A system for reconstructing a three-dimensional representation of a surface topography of an object disposed in a scattering medium, the system comprising:

(a) an acquisition system used to acquire a plurality of scattered signals from multiple regions of the scattering medium and an object disposed in said scattering medium;

(b) a magnitude difference detector used to detect differences among the magnitudes of said plurality of scattered signals obtained from said multiple regions of the scattering medium;

(c) a magnitude correlation system used to correlate differences among the magnitudes of said plurality of scattered signals obtained from said multiple regions with differences in the amount of scattering medium interposed between the object and the scattered signal detector among said multiple regions;

(d) a correlation system used to correlate differences in the amount of scattering medium interposed between the object and the scattered signal detector among said multiple regions with differences in the distance between the object and the scattered signal detector among said multiple regions;

(e) a magnitude calibration system used to create a calibration between the magnitude of a scattered signal and a distance between the object and the scattered signal detector;

(f) a magnitude conversion system used to convert each of said plurality of scattered signal magnitudes into distances between the object and the scattered signal detector; and (g) a three-dimensional representation creation system used to create a three-dimensional representation of the surface topography of the object using the magnitudes of the plurality of scattered signals calibrated to the distance between the object and the scattered signal detector.

38. The system of claim 37, further comprising: a three-dimensional representation creation system for creating a three-dimensional representation of the surface topography of an object having a signal scattering magnitude either less than the scattered magnitude of the scattering medium or greater than the scattered signal magnitude of the scattering medium.

39. The system of claim 37, further comprising: a system for reconstructing a three-dimensional representation of a surface topography of a solid object.

40. The system of claim 37, further comprising: a system for reconstructing a three-dimensional representation of a surface topography of an object disposed in a scattering medium comprising a single phase fluid.

41. The system of claim 37, further comprising: a system for reconstructing a three-dimensional representation of a surface topography of an object disposed in a scattering medium comprising a multi-phase fluid.

42. The system of claim 37, further comprising: an acquisition system used to acquire a plurality of scattered signals from multiple regions of the scattering medium and an object disposed in said scattering medium using an electromagnetic signal scattering detector.

43. The system of claim 37, further comprising: an acquisition system used to acquire a plurality of scattered signals from multiple regions of the scattering medium and an object disposed in said scattering medium using an x-ray signal scattering detector.

44. The system of claim 37, further comprising: an acquisition system used to acquire a plurality of scattered signals from multiple regions of the scattering medium and an object disposed in said scattering medium using a pixelated detector.

45. The system of claim 37, further comprising: an acquisition system used to acquire a plurality of scattered signals from multiple regions of the scattering medium and an object disposed in said scattering medium using an Anger camera.

46. The system of claim 37, further comprising: an acquisition system used to acquire a plurality of scattered signals from multiple regions of the scattering medium and an object disposed in said scattering medium using a plurality of signal scattering detectors.

47. The system of claim 37, further comprising: a magnitude difference detector for detecting differences in the magnitudes of a plurality of scattered signals obtained from an electromagnetic signal source disposed in communication with a plurality of pinhole apertures.

48. The system of claim 37, further comprising: a magnitude difference detector for detecting differences in the magnitudes of a plurality of scattered signals obtained from an electromagnetic signal source disposed in communication with a plurality of coded apertures.

\* \* \* \* \*